(12) United States Patent
Yukimori et al.

(10) Patent No.: US 12,702,292 B2
(45) Date of Patent: Aug. 11, 2026

(54) OPHTHALMOLOGIC APPARATUS

(71) Applicant: TOPCON CORPORATION, Tokyo (JP)

(72) Inventors: Takafumi Yukimori, Tokyo (JP); Yoko Tatara, Tokyo (JP); Makoto Saika, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 196 days.

(21) Appl. No.: 18/368,945

(22) Filed: Sep. 15, 2023

(65) Prior Publication Data

US 2024/0090761 A1 Mar. 21, 2024

(30) Foreign Application Priority Data

Sep. 20, 2022 (JP) ................................ 2022-149310

(51) Int. Cl.

| | |
|---|---|
| ***A61B 3/14*** | (2006.01) |
| ***A61B 3/02*** | (2006.01) |
| ***A61B 3/024*** | (2006.01) |
| ***A61B 3/028*** | (2006.01) |
| ***A61B 3/032*** | (2006.01) |
| ***A61B 3/06*** | (2006.01) |
| ***A61B 3/08*** | (2006.01) |
| ***A61B 3/10*** | (2006.01) |
| ***A61B 3/103*** | (2006.01) |

(52) U.S. Cl.

CPC .............. *A61B 3/103* (2013.01); *A61B 3/022* (2013.01); *A61B 3/024* (2013.01); *A61B 3/028* (2013.01); *A61B 3/032* (2013.01); *A61B 3/063* (2013.01); *A61B 3/08* (2013.01); *A61B 3/10* (2013.01)

(58) Field of Classification Search

CPC ......... A61B 3/103; A61B 3/022; A61B 3/024; A61B 3/028; A61B 3/032; A61B 3/063; A61B 3/08; A61B 3/10

USPC ................................ 351/205, 206, 211, 221

See application file for complete search history.

(56) References Cited

U.S. PATENT DOCUMENTS

| | | | |
|---|---|---|---|
| 2007/0070293 | A1 | 3/2007 | Isogai |
| 2012/0162606 | A1 | 6/2012 | Nakamura |
| 2019/0008380 | A1 | 1/2019 | Hayashi |

FOREIGN PATENT DOCUMENTS

| | | | |
|---|---|---|---|
| JP | 2010082252 | A | 4/2010 |
| JP | 2016159071 | A | 9/2016 |

(Continued)

OTHER PUBLICATIONS

The extended European Search Report from corresponding European Application No. 23197915, mailed on Jan. 30, 2024; 7 pages.

(Continued)

*Primary Examiner* — Mahidere S Sahle
(74) *Attorney, Agent, or Firm* — Tucker Ellis LLP

(57) ABSTRACT

An ophthalmologic apparatus includes an objective measurement optical system that measures an objective refraction characteristic of a subject eye and a control portion that performs total control including control of the objective measurement optical system, wherein the control portion analyzes a characteristic amount of a ring image obtained by measuring the objective refraction characteristic of the subject eye to feedback to a subjective examination content of the subject eye according to an analysis result of the characteristic amount of the ring image.

8 Claims, 10 Drawing Sheets

(56) References Cited

FOREIGN PATENT DOCUMENTS

| | | | | | |
|---|---|---|---|---|---|
| WO | WO-2017135015 | A1 * | 8/2017 | ............... | A61B 3/12 |
| WO | WO-2021049314 | A1 * | 3/2021 | ............. | A61B 3/028 |

OTHER PUBLICATIONS

Japanese Office Action from corresponding Japanese Application No. 2022-149310 mailed on Apr. 7, 6 pages with translation.

* cited by examiner

25L(25R)
E
Ef
1
2
3
4
5
6
7
11
12
13
21
31
41
42
43
44
45
46
51
52
53
54
55
56
57
58
59
61
62
63
63a
63b
64
65
66
67
68
71
72
73
74
75
P
Q
P,Q

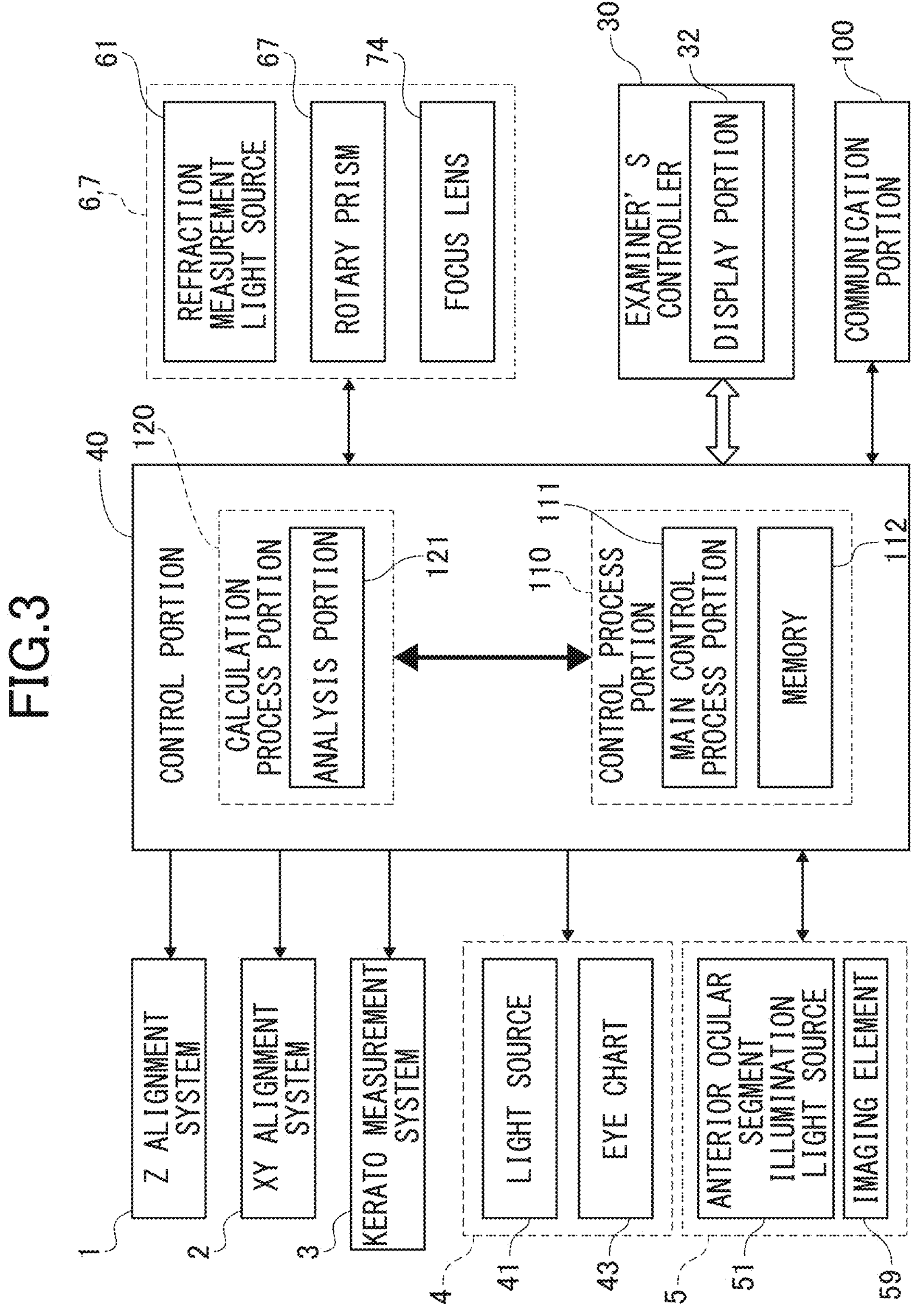
FIG.3
Z ALIGNMENT SYSTEM
XY ALIGNMENT SYSTEM
KERATO MEASUREMENT SYSTEM
LIGHT SOURCE
EYE CHART
ANTERIOR OCULAR SEGMENT ILLUMINATION LIGHT SOURCE
IMAGING ELEMENT
CONTROL PORTION
CALCULATION PROCESS PORTION
ANALYSIS PORTION
CONTROL PROCESS PORTION
MAIN CONTROL PROCESS PORTION
MEMORY
REFRACTION MEASUREMENT LIGHT SOURCE
ROTARY PRISM
FOCUS LENS
EXAMINER'S CONTROLLER
DISPLAY PORTION
COMMUNICATION PORTION
1
2
3
4
41
43
5
51
59
40
120
121
110
111
112
6,7
61
67
74
30
32
100

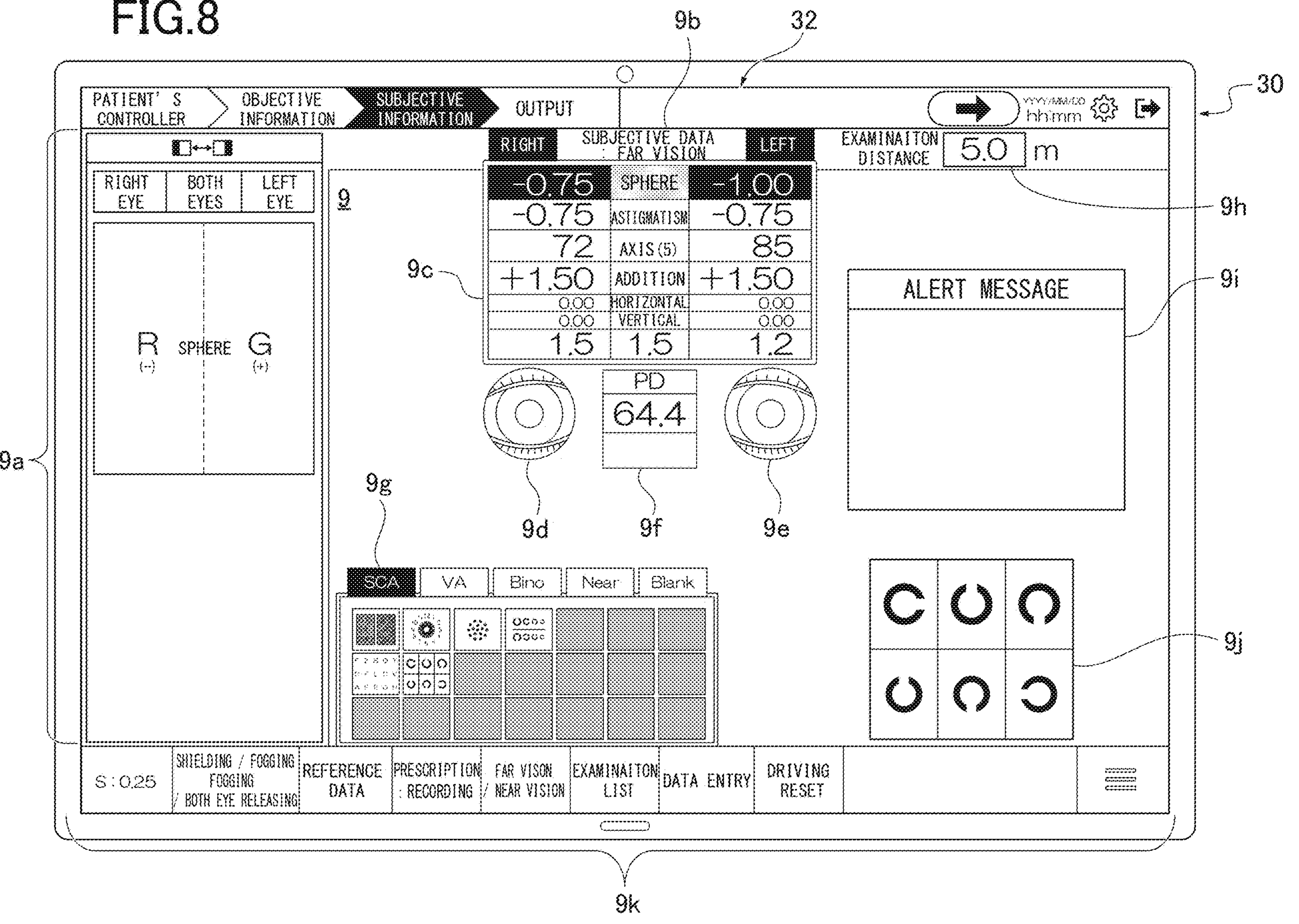
FIG.8
30
32
9b
9a
9c
9d
9e
9f
9g
9h
9i
9j
9k
9
PATIENT' S CONTROLLER
OBJECTIVE INFORMATION
SUBJECTIVE INFORMATION
OUTPUT
YYYY/MM/DD
hh:mm
RIGHT EYE
BOTH EYES
LEFT EYE
R
(-)
SPHERE
G
(+)
RIGHT
SUBJECTIVE DATA : FAR VISION
LEFT
EXAMINAITON DISTANCE
5.0
m
-0.75
SPHERE
-1.00
-0.75
ASTIGMATISM
-0.75
72
AXIS (5)
85
+1.50
ADDITION
+1.50
0.00
HORIZONTAL
0.00
0.00
VERTICAL
0.00
1.5
1.5
1.2
PD
64.4
ALERT MESSAGE
SCA
VA
Bino
Near
Blank
S: 0.25
SHIELDING / FOGGING FOGGING / BOTH EYE RELEASING
REFERENCE DATA
PRESCRIPTION : RECORDING
FAR VISON / NEAR VISION
EXAMINAITON LIST
DATA ENTRY
DRIVING RESET

OPHTHALMOLOGIC APPARATUS

CROSS-REFERENCE TO RELATED APPLICATION

The present application is based on and claims priority from Japanese Patent Application No. 2022-149310 filed on Sep. 20, 2022, the disclosure of which is hereby incorporated by reference in its entirety.

FIELD OF THE INVENTION

The present disclosure relates to an ophthalmologic apparatus.

BACKGROUND

An ophthalmologic apparatus including a projection system that projects light to an ocular fundus of a subject eye, a light receiving system that detects return light from the ocular fundus, an optical system having an optical member that changes a focus condition of an image based on the return light detected by the light receiving system, a display control portion that displays an image on a display portion, an operation portion that changes the focus condition of the image, an optical member control portion that controls an optical member based on an operation content to the operation portion, and a calculation portion that calculate subject eye information based on an image and a control content to an optical member is conventionally known (see JP2016-159071A, for example).

SUMMARY

When a subject eye has an ametropia (e.g., cataract and high order aberration eye), for example, the best eyesight may be lowered than that of a normal subject eye, a response of an astigmatism examination may be no good, and an error may occur in automatic subjective examination. An object of the conventional art described in JP2016-159071A is to acquire subject eye information such as refractive power even though the subject eye has a disease. For this reason, when the subject eye has an ametropia, the conventional art has a problem that cannot previously handle a problem that may occur during the subjective examination.

The present disclosure has been made in view of the above circumstance, and an object of the present disclosure is to provide an ophthalmologic apparatus capable of previously dealing with a problem that may occur during subjective examination.

In order to achieve the object described above, an ophthalmologic apparatus includes an objective measurement optical system that measures an objective refraction characteristic of a subject eye; and a control portion that performs total control including control of the objective measurement optical system, wherein the control portion analyzes a characteristic amount of a ring image obtained by measuring the objective refraction characteristic of the subject eye to feedback to a subjective examination content of the subject eye according to an analysis result of the characteristic amount of the ring image.

BRIEF DESCRIPTION OF DRAWINGS

FIG. 3 is a block diagram illustrating a configuration example of a control system of the ophthalmologic apparatus of the first embodiment.

FIG. 8 is a view illustrating one example of a subject examination screen that is displayed on the display portion of the examiner's controller in subjective examination.

DETAILED DESCRIPTION

Figure 1:
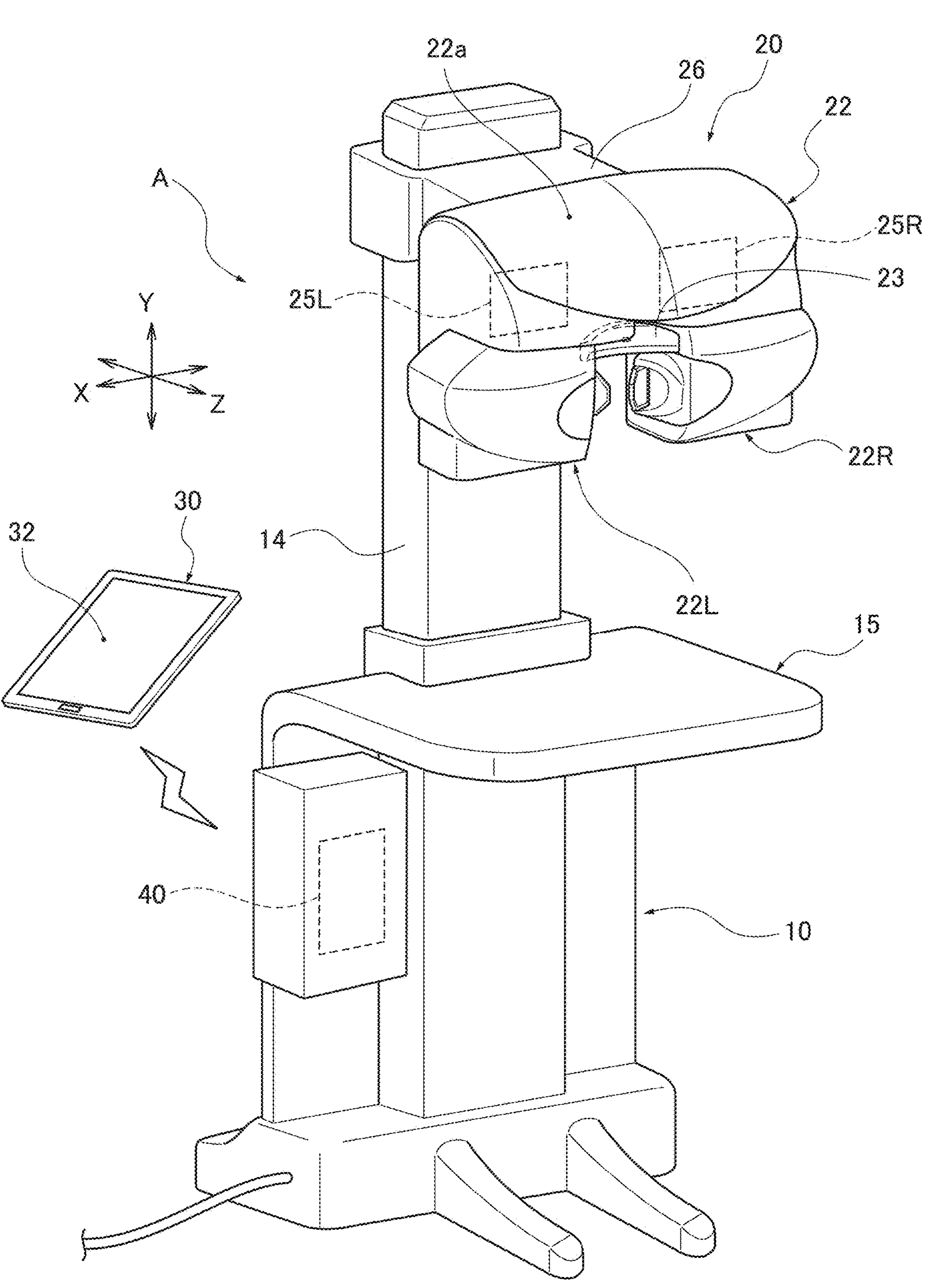
FIG. 1 is a perspective view illustrating an entire configuration of an ophthalmologic apparatus of a first embodiment.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

An embodiment of an ophthalmologic apparatus according to the present disclosure will be described based on first to third embodiments illustrated in the figures. The first and second embodiments are application examples to the ophthalmologic apparatus having an objective measurement function and a subjective examination function of a subject eye. The third embodiment is an application example to an ophthalmologic system having an objective measurement device and a plurality of subjective examination devices. In each figure, an axis in a left and righty direction represents a left and right axis X, an axis in an up and down direction (axis in vertical direction) represents an up and down axis Y, and an axis in a depth direction orthogonal to the left and right axis X and the up and down direction Y represents a front and back direction Z when facing the ophthalmologic apparatus with the subject eye E as a standard.

First Embodiment

An entire configuration of an ophthalmologic apparatus A of the first embodiment will be described with reference to FIG. 1. The ophthalmologic apparatus Aincludes a support base 10, a measurement unit 20, an examiner's controller 30, and a control portion 40.

The ophthalmologic apparatus Ais an objective measurement device with a subjective examination function having a subjective examination optical system, an objective measurement optical system, a phoropter, and an optotype. That is, an examiner performs voluntary objective measurement and subjective examination with the ophthalmologic apparatus A. In the objective measurement, a subject eye E is irradiated with light, and the objective measurement information regarding the subject eye E is acquired based on the detection result of the return light.

The objective measurement includes measurement for acquiring an eye characteristic of the subject eye E and photographing for acquiring an image of the subject eye E. The objective measurement includes refraction measurement, corneal shape measurement (kerato measurement), intraocular pressure measurement, and ocular fundus photographing. In the subjective test, for example, an eye chart is presented to a patient, and the information (eye characteristic) regarding the subject eye (E) is acquired based on the response of the patient to the presented eye chart. The subjective examination includes far examination, intermediate examination, near examination, contrast examination, subjective refraction examination such as glare examination, and visual field examination.

The support base 10 includes a column 14 rising from a floor and a table 15 for optometry supported by the column 14. A device and a tool for use in optometry such as the examiner's controller 30 are placed on the table 15, and the table 15 also supports a posture of a patient. The position (height position) of the table 15 in the Y direction may be fixed and the position (height position) of the table 15 in the Y direction may be adjustably supported by the column 14.

The measurement unit 20 includes an arm 26, a measurement head 22, and a forehead rest 23. One end of the arm 26 is supported by a leading end portion of the column 14, and the other end of the arm 26 extends toward a patient from the column 14 along the Z direction, and the measurement head 22 is attached to the leading end portion of the arm 26. The measurement head 22 is thereby hung on the column 14 through the arm 26 above the table 15. The arm 26 is movable in the Y direction relative to the column 14. The arm 26 may be movable in the X direction and Z direction relative to the column 14.

The measurement head 22 measures an eye characteristic of the subject eye E. The measurement head 22 includes a driving portion 22*a*, and a pair of a left measurement head portion 22L and a right measurement head portion 22R that are provided under the driving portion 22*a*. The left measurement head portion 22L and the right measurement head portion 22R correspond to the left and right eyes of the patient, respectively. A left eye optical system 25L that measures the eye characteristic of the left subject eye E of the patient is built in the left eye optical system 25L. Aright eye optical system 25R that measures an eye characteristic of the right subject eye E is built in the right eye optical system 25R. The measurement result by the measurement head 22 is input to the control portion 40.

The driving portion 22*a* drives the left measurement head portion 22L and the right measurement head portion 22R horizontally (X direction) and vertically (Y direction), and rotates the left measurement head portion 22L and the right measurement head portion 22R in the X direction and the Y direction.

The forehead rest 23 is provided in the measurement unit 20, and is disposed between the left measurement head portion 22L and the right measurement head portion 22R. The forehead rest 23 supports a face of a patient when a forehead of a patient contacts the forehead rest 23 during the measurement of the eye characteristic. That is, the patient facing the table 15 presses his or her forehead onto the forehead rest 23 to be stabilized such that the direction and the position of the face do not move. The position of the forehead rest 23 is adjusted by moving the arm 26 in the Y direction relative to the column 14.

The examiner's controller 30 is an information processing device that receives the input operation by an examiner and outputs a control signal to the control portion 40. The examiner's controller 30 is a tablet terminal and a smart phone, for example, and is separated from the measurement unit 20 and is portable by an examiner. The examiner's controller 30 may be a laptop computer, a desktop computer, or a controller dedicated to the ophthalmologic apparatus A. The examiner's controller 30 exchanges information with the control portion 40 via wireless communication and network communication.

As illustrated in FIG. 1, the examiner's controller 30 includes a display portion 32, a not-illustrated operation control portion, and a not-illustrated input button. The display portion 32 is a touch panel display provided on the surface of the examiner's controller 30, and various input buttons are set by the screen display. The operation control portion is a microcomputer built in the examiner's controller 30, and controls an image that is displayed on the display portion 32 based on the measurement result and the detection result sent from the control portion 40, and outputs the control signal according to the operation to the input bottom to the control portion 40.

The control portion 40 is an information processing device provided under the table 15, for example. The control portion 40 totally controls each portion of the measurement unit 20 based on the control signal sent from the examiner's controller 30. The control portion 40 sends the measurement result of the eye characteristic of the subject eye E measured by the measurement head 22 to the examiner's controller 30. The detailed configuration of the control system including the control portion 40 will be described later.

The configuration of the optical system (left eye) built in the measurement head 22 will be described with reference to FIG. 2. As the left eye optical system 25L and the right eye optical system 25R have the same configuration, hereinbelow, the left eye optical system 25 will be only described, and the figure and the description of the right eye optical system 25R will be omitted.

"Ocular fundus conjugate position" for use in the following description is a position that is optically and substantially conjugated with the ocular fundus Ef of the subject eye E in an alignment condition, and is meant to be a position optically conjugated with the ocular fundus Ef of the subject eye E and a position near that position. "Pupil conjugate position" is a position that is optically and substantially conjugated with the pupil of the subject eye E in an alignment condition, and is meant to be a position that is optically conjugated with the pupil of the subject eye E and a position near that position.

Figure 2:
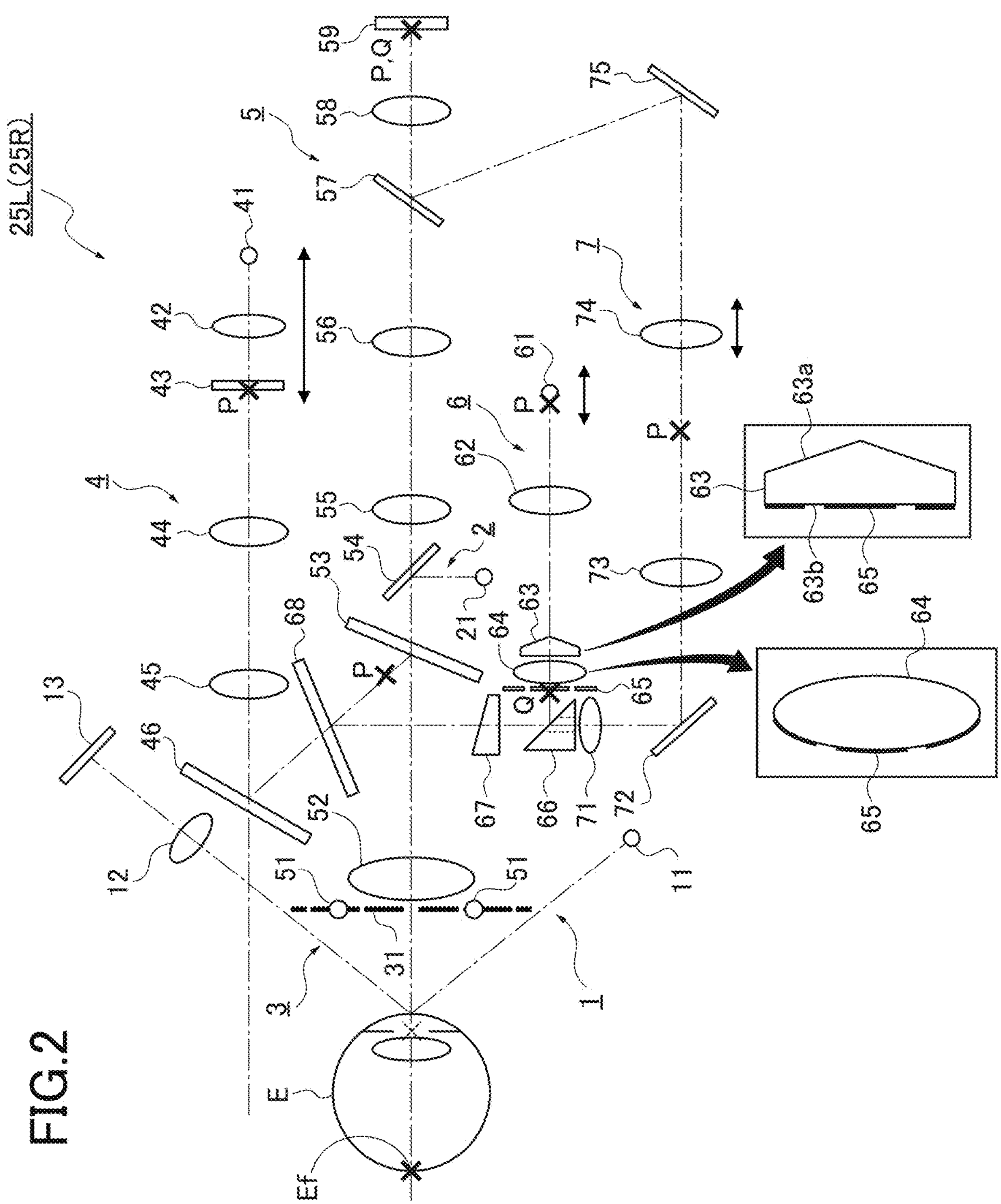
FIG. 2 is a schematic view illustrating a configuration example of an optical system (left eye) of the ophthalmologic apparatus of the first embodiment.

The left eye optical system 25L for examining the subject eye E includes a Z alignment system 1, an XY alignment system 2, a kerato measurement system 3, an eye chart projection system 4, an anterior ocular segment observation system 5, a refraction measurement projection system 6, and a refraction measurement light receiving system 7, as illustrated in FIG. 2.

The Z alignment system 1 projects light (infrared light) for aligning in the optical axis direction (front and back direction, Z direction) of the anterior ocular segment observation system 5 to the subject eye E. The light output from the Z alignment light source 11 is projected to the cornea of the subject eye E, is reflected by the cornea, and is imaged on the sensor surface of the line sensor 13 by the imaging lens 12. When the position of the corneal apex is changed in the optical axis direction of the anterior ocular segment observation system 5, the projection position of the light in the sensor surface of the line sensor 13 is changed. The control portion 40 acquires the position of the corneal apex of the subject eye E based on the projection position of the light in the sensor surface of the line sensor 13, and performs the Z alignment by controlling a mechanism for moving the optical system based on the acquired position.

The XY alignment system 2 irradiates light (infrared light) for the alignment in the direction orthogonal to the optical axis of the anterior ocular segment observation system 5 (left and right direction (=X direction), the up and down direction (=Y direction) to the subject eye E. The XY alignment system 2 includes an XY alignment light source 21 provided in an optical path branched from the anterior ocular segment observation system 5 by the half mirror 54. The light output from the XY alignment light source 21 is reflected on the half mirror 54, and is projected to the subject eye E through the anterior ocular segment observation system 5. The reflection light by the corneal of the subject eye E is guided to the imaging element 59 through the anterior ocular segment observation system 5. The image (bright spot image) based on the reflection light is included in the anterior ocular segment image. The control portion 40 displays the anterior ocular segment image including the bright spot image and the alignment mark on the display portion 32. When the XY alignment is manually performed, a user performs an operation for moving the optical system to guide the bright image in the alignment mark. When the alignment is automatically performed, the control portion 40 controls a mechanism for moving the optical system to cancel the displacement of the bright point image to the alignment mark.

The kerato measurement system 3 projects a ring light flux (infrared light) for measuring the shape of the corneal of the subject eye E to a cornea. The kerato plate 31 is disposed between the objective lens 52 and the subject eye E. A not-illustrated kerato ring light source is provided rear of the kerato plate 31 (objective lens 52 side). The ring light flux is projected to the cornea of the subject eye E by illuminating the kerato plate 31 with the light from the kerato ring light source. The reflection light from the cornea of the subject eye E (kerato ring image) is detected together with the anterior ocular segment image by the imaging element 59. The control portion 40 calculates a corneal shape parameter showing the shape of the cornea with a known calculation based on the kerato ring image.

The eye chart projection system 4 presents various eye charts such as a fixed eye chart and an eye chart for a subjective examination to the subject eye E. The light (visible light) output from the light source 41 is converted into a parallel light flux by the collimate lens 42, and is irradiated to the eye chart 43. The eye chart 43 includes, for example, a transmission type liquid crystal panel, and displays a patter representing an eye chart. The light transmitted through the eye chart 43 passes through the relay lenses 44, 45, is reflected on the reflection mirror 46, transmits through the dichroic mirror 68, and is reflected by the dichroic mirror 53. The light reflected by the dichroic mirror 53 passes through the objective lens 52, and is projected onto the ocular fundus Ef. The light source 41, the collimate lens 42, and the eye chart 43 are integrally movable in the optical axis direction.

When performing the subjective examination, the control portion 40 moves the light source 41, the collimate lens 42, and the eye chart 43 in the optical axis direction based on the result of the objective measurement, and controls the eye chart 43. The control portion 40 displays the eye chart selected by an examiner or the control portion 40 to the eye chart 43. The eye chart is thereby presented to a patient. The patient responds to the eye chart. Upon the input of the response content, the control portion 40 further controls or calculates the subjective examination value. For example, in vision measurement, the control portion 40 selects a next eye chart based on the response to a Landolt ring to be presented, and determines a visual acuity value by repeating this process.

The anterior ocular segment observation system 5 photographs the moving image of the anterior ocular segment of the subject eye E. In the optical system through the anterior ocular segment observation system 5, the imaging face of the imaging element 59 is disposed in the pupil conjugated position Q. The anterior ocular segment illumination light source 51 irradiates the illumination light (e.g., infrared light) to the anterior ocular segment of the subject eye E. The light reflected by the anterior ocular segment of the subject eye E passes through the objective lens 52, transmits through the dichroic mirror 53 and the half mirror 54, passes through the relay lenses 55, 56, and transmits through the dichroic mirror 57. The light transmitted through the dichroic mirror 57 is imaged on the imaging surface of the imaging element 59 (area sensor) by the imaging lens 58. The imaging element 59 images and outputs a signal at a predetermined rate. The output of the imaging element 59 (image signal) is input to the control portion 40. The control portion 40 displays the anterior ocular segment image based on the image signal on the display portion 32 of the examiner's controller 30. The anterior ocular segment image is an infrared light moving image, for example.

The refraction measurement projection system 6 and the refraction measurement light receiving system 7 are used in the objective refraction measurement (refraction measurement). The refraction measurement projection system 6 projects the ring light flux (infrared light) for objective measurement to the ocular fundus Ef. The refraction measurement light receiving system 7 receives the return light of the ring light flux from the subject eye E.

The refraction measurement light source 61 may be a Super Luminescent Diode (SLD) light source that is a high brightness light source having a light emitting diameter with a predetermined size or blow. The refraction measurement light source 61 is movable in the optical axis direction, and is disposed in the ocular fundus conjugated position P. A ring diaphragm 65 (more specifically, transmission portion) is disposed in the pupil conjugated position Q. A focus lens 74 is movable in the optical axis direction. The focus lens 74 may be a known focus variable lens that receives control from the after-described main control process portion 111 and a focused position is changeable. In the optical system through the refraction measurement light receiving system 7, the imaging face of the imaging element 59 is disposed in the ocular fundus conjugated position P.

The light output from the refraction measurement light source 61 passes through the relay lens 62, and enters a cone face of a cone prism 63. The light entered the cone face is deflected, and emits from the bottom face of the cone prism 63. The light emitted from the bottom face of the cone prism

63 passes through a field lens 64, and passes through the transmission portion formed in a ring shape in the ring diaphragm 65. The light (ring light flux) passed through the transmission portion of the ring diaphragm 65 is reflected by the reflection face of a holed prism 66, passes through a rotary prism 67, and is reflected by the dichroic mirror 68. The light reflected by the dichroic mirror 68 is reflected by the dichroic mirror 53, passes through an objective lens 52, and is projected onto the subject eye E. The rotary prism 67 is used to average the light volume distribution of the ring light flux to the blood vessel or the disease site of the ocular fundus Ef and to reduce the speckle noise due to the light source. The cone prism 63 is preferably disposed in a position closer to the pupil conjugated position Q as much as possible.

The field lens 64 has a lens face on the subject eye E side, and the ring diaphragm 65 is attached to the lens face of the field lens 64 as illustrated in FIG. 2. In this case, a light shielding film is deposited to the lens face of the field lens 64 to form a ring transmission portion, for example. The refraction measurement projection system 6 may include the field lens 64 having an omitted configuration.

As illustrated in the right blasted view of FIG. 2, the cone prism 63 has a cone face 63*a* that the light passed through the relay lens 62 enters, and a bottom face 63*b* on which the ring diaphragm 65 is attached. In this case, for example, the light shielding film is deposited onto the bottom face 63*b* of the cone prism 63 to form the ring transmission portion. The ring diaphragm may be provided on the cone face 63*a* side of the cone prism 63. The ring diaphragm 65 may be a diaphragm in which the transmission portion having a shape corresponding to a predetermined measurement pattern is formed. The transmission portion may be formed in the diaphragm in a position eccentric to the optical axis of the refraction measurement projection system 6. The two or more transmission portions may be formed in the diaphragm.

The return light of the ring light flux projected onto the ocular fundus Ef passes through the objective lens 52, and is reflected by the dichroic mirror 53 and the dichroic mirror 68. The return light reflected by the dichroic mirror 68 passes through the rotary prism 67, passes through the holed prism 66, passes through the relay lens 71, is reflected by the reflection mirror 72, and passes through the relay lens 73 and the focus lens 74. The light passed through the focus lens 74 is reflected by the reflection mirror 75, is reflected by the dichroic mirror 57, and is imaged as a "ring image" on the imaging face of the imaging element 59 by the imaging lens 58. The control portion 40 calculates a refractive power value of the subject eye E by executing known calculation based on the output from the imaging element 59. For example, the refractive power value includes the spherical power, astigmatic power, and astigmatism axis angle. A diaphragm that controls the light flux diameter on the pupil is disposed between the holed prism 66 and the relay lens 71. This transmission portion of the diaphragm is disposed in the pupil conjugated position.

The control portion 40 moves the refraction measurement light source 61 and the focus lens 74 in the optical axis direction such that the ocular fundus Ef, the refraction measurement light source 61, and the imaging face of the imaging element 59 are optically conjugated based on the calculated refraction power value. The control portion 40 moves the eye chart unit in the optical axis direction in connection with the movement of the refraction measurement light source 61 and the focus lens 74. The light source 41, the collimate lens 42, the eye chart unit including the eye chart 43, the refraction measurement light source 61, and the focus lens 74 are movable in conjunction with the respective optical axes.

As described above, in the optical system of the ophthalmologic apparatus A, the refraction measurement light source 61 is disposed in the ocular fundus conjugated position P, the ring diaphragm 65 is disposed in the pupil conjugated position Q, and the cone prism 63 is disposed near the pupil conjugated position Q. Athin (width between inner diameter and outer diameter is narrow) and high brightness ring measurement pattern can be thereby projected onto the ocular fundus Ef. Accordingly, the high brightness measurement pattern light flux can be projected onto the subject eye while reducing the entire light volume of the measurement light flux entering the subject eye E and the load of a patient. A highly reliable eye reflective power value can be thereby acquired. As the profile of the ring image in the ocular funds becomes steep, the influence by the shielding of the incident light flux in the cloud portion of the lens eye due to eyelash and cataract can be reduced, so that the occurrence of the measurement error can be controlled.

The configuration of the control system of the ophthalmologic apparatus A will be described with reference to FIG. 3. The control portion 40 totally controls each portion of the ophthalmologic apparatus A. The control portion 40 can execute various calculation processes. The control portion 40 includes a processor. The function of the processor is achieved by a circuit such as a Central Processing Unit (CPU), a Graphics Processing Unit (GPU), and an Application Specific Integrated Circuit (ASIC). The control portion 40 achieves the operation according to the present disclosure by reading the program stored in a memory circuit and a memory.

The control system of the ophthalmologic apparatus A includes the examiner's controller 30, the control portion 40, the communication portion 100 in addition to the optical system configuration (Z alignment system 1 to refraction measurement light receiving system 7), as illustrated in FIG. 3. The control portion 40 includes a control process portion 110 and a calculation process portion 120.

The control process portion 110 controls each portion of the ophthalmologic apparatus A. The control process portion 110 includes the main control process portion 111 and the memory 112.

The main control process portion 111 controls the Z alignment light source 11 and the line sensor 13 of the Z alignment system 1, the XY alignment light source 21 of the XY alignment system 2, and the kerato ring light source of the kerato measurement system 3. The light volume of the light output from the Z alignment light source 11, the XY alignment light source 21, and the kerato ring light source is thereby changed and the lighting and the non-lighting is thereby switched. The signal detected by the line sensor 13 is loaded, and the alignment control based on the loaded signal is performed.

The main control process portion 111 controls the light source 41 of the eye chart projection system 4 and the eye chart 43. The light volume of the light output from the light source 41 is thereby changed and the lighting and non-lighting is thereby switched. The turning on and off of the display of the eye chart and the fixed eye chart on the eye chart 43 is also switched and the eye chart and the fixed eye chart is switched. The main control process portion 111 can control a non-shown movement mechanism that moves the light source 41, the collimate lens 42, and the eye chart unit including the eye chart 43 in the optical axis direction.

The main control process portion 111 controls the anterior ocular segment illumination light source 51 and the imaging element 59 of the anterior ocular segment observation system 5. The volume of the light output from the anterior ocular segment illumination light source 51 is thereby changed and the lighting and non-lighting are switched. The detection sensibility is changed by changing the exposure time of the imaging element 59 and controlling the gain of the amplifier in the imaging element 59. The signal acquired by the imaging element 59 is loaded, and the image is formed by the calculation process portion 120.

The main control process portion 111 controls the refraction measurement light source 61 and the rotary prism 67 of the refraction measurement projection system 6 and the focus lens 74 of the refraction measurement light receiving system 7. The volume of the light output from the refraction measurement light source 61 is thereby changed and the lighting the non-lighting are switched. The rotation speed of the rotary prism 67 is changed, and the turning on and off of the rotation operation are switched. The position of the focus lens 74 in the optical axis direction is also changed. The main control process portion 111 can control a not-shown movement mechanism that moves the refraction measurement light source 61 and the focus lens 74 in the optical axis direction. When the focus lens 74 is a variable focus lens, the main control process portion 111 can change the focused position of the focus lens 74 by controlling the focus lens 74.

In the first embodiment, the main control process portion 111 can control the light source 41, the collimate lens 42, and the movement mechanism including the holding member that holds the eye chart having the eye chart 43, the refraction measurement light source 61, and the focus lens 74. The movement mechanism is provided with an actuator that generates a driving force for moving the holding member and the transmission mechanism that transmits the driving force. The actuator includes a pulse motor, for example. The transmission mechanism includes a combination of gears and a lack and pinion, for example. The main control process portion 111 controls such movement mechanism to move each portion in the optical axis direction.

The main control process portion 111 controls the eye chart projection system 4, the anterior ocular segment observation system 5, the refraction measurement projection system 6, the refraction measurement light receiving system 7, and the calculation process portion 120 to perform temporary measurement two times or more, and to perform the regular measurement under the measurement condition determined by the finally performed temporary measurement. The measurement condition of the same type may be determined by the temporary measurement of each time to settle the measurement condition by repeating the temporary measurement, or the measurement condition of the different type may be determined.

The main control process portion 111 executes the process that writes data in the memory 112 and the process that reads out the data from the memory 112.

The memory 112 stores data. The data stored in the memory 112 includes the measurement information acquired by the kerato measurement system 3, the measurement information acquired by the refraction measurement projection system 6 and the refraction measurement light receiving system 7, the image data of the image acquired by the imaging element 59, and the subject eye information. The subject eye information includes information regarding a patient such as a patient's ID and name and identification information of a left eye and a right eye. The measurement information acquired by the kerato measurement system 3 is stored in the memory 112 when the kerato measurement of the subject eye E is performed in the ophthalmologic apparatus A. The measurement information acquired by the refraction measurement projection system 6 and the refraction measurement light receiving system 7 are stored in the memory 112 when the refraction measurement of the subject eye E is performed in ophthalmologic apparatus A. The memory 112 may be used as a working memory of the calculation process of the corneal shape parameter and the calculation process of the eye refractive power value. The memory 112 stores various programs and data for operating the ophthalmologic apparatus A.

The calculation process portion 120 executes the various calculations for obtaining the corneal shape parameter and the parameter showing the eye refractive power such as an eye refractive power value. The calculation process portion 120 includes an analysis portion 121.

The analysis portion 121 analyzes the ring image obtained by receiving with the imaging element 59 the return light of the ring light flux (ring measurement pattern) projected onto the ocular fundus Ef by the refraction measurement projection system 6. For example, the analysis portion 121 obtains a ring center position of the ring image based on the brightness distribution in the image on which the obtained ring image is visualized, and obtains the brightness distribution along a plurality of scanning directions radially extending from the ring center position, so as to specify the ring image based on the brightness distribution. The analysis portion 121 determines whether or not the brightness of the specified ring image (ring brightness) is within a predetermined brightness range. The analysis portion 121 may determine whether or not a SN ratio of the specified ring image is within a predetermined numerical value range.

The analysis portion 121 obtains the approximate ellipse of the specified ring image to obtain the spherical power, the astigmatism power, and the astigmatism axis angle by substituting the long diameter and the short diameter of the approximate ellipse into a known formula. Alternatively, the analysis portion 121 obtains the spherical power, the astigmatism power, and the astigmatism axis angle based on the control content (e.g., movement amount) to the focus lens 74 and the specified ring image (approximate ellipse). Alternatively, the analysis portion 121 obtains the parameter of the eye reflective power based on the deformation and the displacement of the ring image to the standard pattern.

The analysis portion 121 calculates the corneal refractive power, the corneal astigmatism power, and the corneal astigmatism angle based on the kerato ring image acquired by the anterior ocular segment observation system 5. For example, the analysis portion 121 calculates the corneal curvature radius of the steeper meridian and the flatter meridian of the corneal front face by analyzing the kerato ring image to calculate the above parameter based on the corneal curvature radius.

The analysis portion 121 further analyzes the feature amount of the ring image in addition to obtaining the spherical power, the astigmatism power, and the astigmatism axis angle based on the ring image. The analysis of the feature amount of the ring image and the feedback determination that reflects the analysis result to the subjective examination will be described in details later.

The examiner's controller 30 receives the control by the control process portion 110 to display on the display portion 32 the information. The screen display content on the display portion 32 includes various software keys (e.g., button, icon, menu) for use in the operation and information input of the ophthalmologic apparatus A. The screen display content on the display portion 32 further includes an alert message to an examiner.

The communication portion 100 includes a function of communicating with an external device. The communication portion 100 includes a communication interface according to a connection condition with an external device. The external device includes as an example an eyeglass lens measurement device that measures an optical characteristic of a lens. The eyeglass lens measurement device measures a power of an eyeglass lens that is worn by a patient, and input the measurement data to the ophthalmologic apparatus A. The external device may be a device (reader) that reads information from a recoding medium and a device (writer) that writes writing information to a recording medium. The external device may be a hospital information system (HIS) server, a Digital Imaging and Communication in Medicine (DICOM) server, a doctor terminal, a mobile terminal, an individual terminal, and a cloud server.

Figure 4:
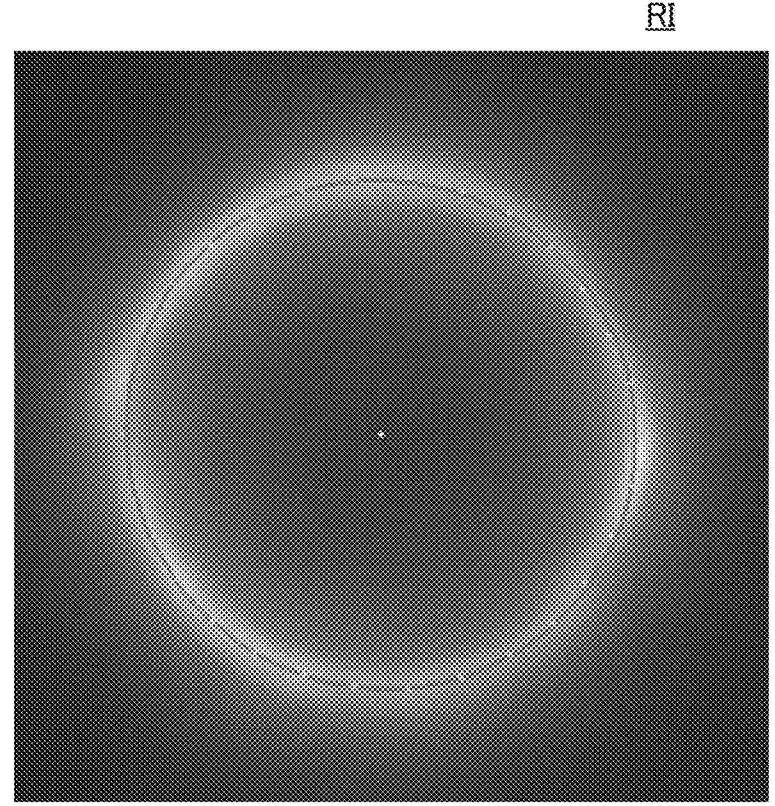
FIG. 4 is a view illustrating an image example of a ring image as an analysis target of a characteristic amount.
Figure 5:
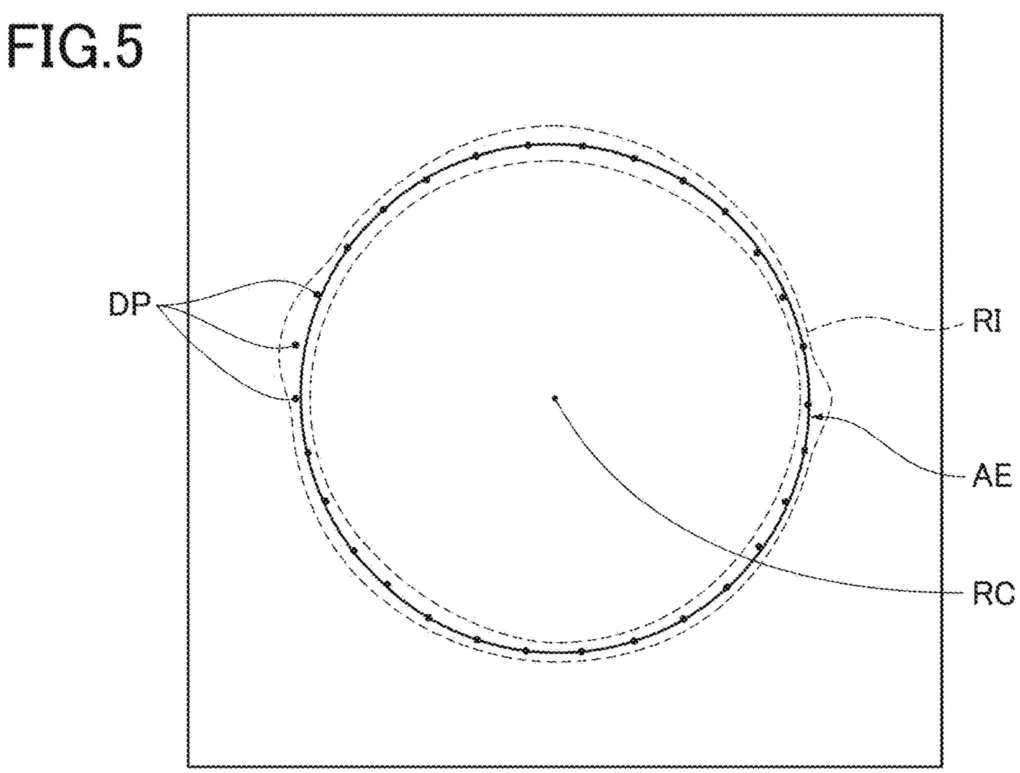
FIG. 5 is an explanatory diagram showing each name of the ring image as the analysis target of the characteristic amount.

The characteristic amount of the ring image, the analysis of the characteristic amount, and the feedback determination to the subjective examination will be described with reference to FIGS. 4, 5. FIG. 4 illustrates an image example of a ring image that is an eye chart of characteristic amount analysis. FIG. 5 illustrates each name of the ring image. The ring image is referred to as RI, the detection point is referred to as DP, the approximate ellipse is referred to as AE, and the center coordinate is referred to as RC.

The characteristic amount of the ring image RI obtained by measuring the objective refractive characteristic is as follows.

(1) Brightness of ring image RI
(2) Edge intensity of ring image RI
(3) Contrast of ring image RI
(4) Width of ring image RI
(5) Residual to approximate ellipse AE of detection point DP of ring image RI
(6) Number of detection points DP of ring image RI
(7) One item or combination of a plurality of items of center coordinate CP of approximate ellipse AE of detection point DP of ring image RI In the first embodiment, when analyzing the characteristic amount of the ring image RI obtained by the measurement of the objective refractive characteristic, a reliability coefficient SC based on a score value showing a reliability with a subjective examination is calculated for one item or the combination of a plurality of items of the characteristic amount of the ring image. More specifically, a higher reliability coefficient SC shows a lower probability of an occurrence of a problem in a subject examination while a lower reliability coefficient SC shows a higher probability of an occurrence of a problem in a subjective examination. For example, when all items of the above seven items are the characteristic amount of the ring image RI, the weighted sum or the total sum of the score value Z1, Z2, Z3, Z4, Z5, Z6, Z7 of each item is calculated as the reliability coefficient SC. When selecting two to six items from the above seven items, the weighted sum or the total sum of the score values of the selected item is calculated as the reliability coefficient SC. When one item is selected, the score value of the selected one item is used as the reliability coefficient SC.

When the calculated reliability coefficient SC is a value that is a normal determination value or more, the feedback of the analysis result of the characteristic amount of the ring image RI is set to no feedback. On the other hand, when the reliability coefficient SC is a value less than the normal determination value, the feedback of the analysis result of the characteristic amount of the ring image RI is set to feedback.

Note that the normal determination value may ben given to each of the score value of the seven items that are the characteristic amounts of the ring image RI in addition to the reliability coefficient SC with the total sum of the score value or the weighting sum of the score value. In this case, when a plurality of items is selected as the characteristic amount of the ring image RI, if the score value of one item is less than the normal determination value even if the reliability coefficient SC with the total sum of the score value is the normal determination value or more, the feedback is set. Hereinafter, the relationship between each characteristic amount and the score value (reliability coefficient SC) will be described.

As to (1) the brightness of the ring image RI, when the ring image RI darkens due to decrease (e.g., cataract) in a transmission of an intermediate transmission body of the subject eye E and an individual difference of reflecting power of a retina, the SN ratio in analysis is lowered, and the measurement accuracy may be lowered. Accordingly, a higher brightness score value Z1 is given as the brightness of the ring image RI increases and a lower brightness score value Z1 is given as the brightness of the ring image RI decreases.

As to (2) the edge intensity of the ring image RI, when the refraction projection light is scattered by the cloud (cataract) of the intermediate transmission body of the subject eye E, the ring image RI becomes unclear, and the edge becomes unclear. This is the same as when the ring image RI is not focused. When the edge becomes unclear as described above, it becomes difficult to divide the portion that is the ring image RI and the portion that is not the ring image RI, and the detection error may increase. Accordingly, a higher edge strength score value Z2 is a higher value as the edge of the ring image RI sharpens and a lower edge strength score value Z2 is given as the edge of the ring image RI blunts.

As to the contrast of the ring image RI (3), when the refraction projection light scatters by the cloud (e.g., cataract) of the intermediate transmission body of the subject eye E, the difference in brightness and darkness of the periphery of the ring image RI and the ring image RI is reduced. When the difference in brightness and darkness is lowered, similar to (1), the measurement accuracy may be lowered due to decrease in a SN ratio. Accordingly, a higher contrast score value Z3 is given as the difference in brightness and darkness of the ring image RI increases and a lower contrast score value Z3 is given as the difference in brightness and darkness of the ring image RI decreases.

As to the width of the ring image RI (4), the width of the ring image RI detected when the ring image RI is unclear thickens. The detection error may increase as the width of the ring image RI thickens. Accordingly, a higher width score value Z4 is given as the width of the ring image RI thins and a lower width score value Z4 is given as the width of the ring image RI thickens. When the width of the ring image RI varies, the average point of the image width at each detection point DP is given.

As to the residual to the approximate ellipse AE of the detection point DP of the ring image RI (5), when the subject eye E has irregular astigmatism, for example, the ring image RI is distorted, and deviates from an ellipse shape. Although SCA (S: spherical power, C: astigmatism power, A: astigmatism axis) are calculated by approximating to an ellipse in the analysis, the residual of the detection point DP and the approximate ellipse AE increases as the shape of the original ring image RI deviates from the approximate ellipse AE. The refractive condition of the subject eye E cannot be accurately shown if this value is large. Accordingly, a higher residual score value Z5 is given as the residual of the approximate ellipse AE of the detection point DO decreases and a lower residual score value Z5 is given as the residual of the approximate ellipse AE of the detection point DO increases. That is, the radial direction distance between each detection point DP and the approximate ellipse AE determined based on the detection point DP is a residual, and the reliability coefficient SC is reflected by using the sum of square of this residual.

As to the number of the detection points DP of the ring image RI (6), in analysis, for example, 360 longitudinal lines are drawn from the ring center RC at 1° intervals to obtain an intersection point (weighted position) with the refraction at each longitudinal line. When the ring image RI is chipped due to the decrease in transmission (e.g., cataract) of the intermediate transmission body of the subject eye E, the number of the detection points DP to be detected is reduced. The analysis error may increase as the number of detection points DP (sampling point) decreases. Accordingly, a higher detection point score value Z6 is given when the number of the detection points DP coincides with the number of the longitudinal lines and a lower detection point score value Z6 is given as the number of detection points DP reduces from the number of longitudinal lines.

As to the center coordinate CP of the approximate ellipse AE of the detection point DP of the ring image RI (7), when the subject eye E is displaced from the device optical axis, the ring image RI is displaced from the standard position BP of the device. The standard position BP includes the center coordinate of the ring image RI when the position of the subject eye E is aligned with the device optical axis. When the subject eye E is displaced from the device optical axis, the measurement is performed with the axis misaligned with the optical axis of the subject eye, so that the measurement accuracy may be lowered. Accordingly, a higher center coordinate score value Z7 is given as the displacement from the standard position BP of the center coordinate CP of the ring image RI decreases and a lower center coordinate score value Z7 is given as the displacement from the standard position BP of the center coordinate CP of the ring image RI increase.

The feedback control process operation that feedbacks the characteristic amount analysis result of the ring image RI of the subject eye E to the subject examination will be described with reference to FIGS. 6 to 8. Note that the examination starts when a patient sits in front of the ophthalmologic apparatus A, and the visual line of the subject eye E is fixed to the fixed eye chart.

Step S1 is the preliminary measurement that brings the subject eye E into focus in a fogging start position, and is performed in the following procedure, for example. More specifically, the control portion 40 calculates the temporary spherical power S and cylindrical power C of the subject eye E based on the image of the ring image obtained by the refraction measurement projection system 6 and the refraction measurement light receiving system 7. The control portion 40 controls the position of the focus lens 74 based on the calculation result of the temporary spherical power S and cylindrical power C to move the focused position of the pattern light to the position (position corresponding to temporary far point: fogging start position) corresponding to the equivalent spherical power (S+C/2). The fogging method is meant to be a method of performing a refraction test in an unfocused near site condition, so as to prevent the interference of the adjustment power by the subject eye E. The fogging amount from the fogging start position is presented as a presentation position (presented distance) of the fixed eye chart.

In Step S2, following the preliminary measurement in Step S1, the fogging control is performed, and the process proceeds to Step S3. In this case, "fogging control" is mean to monitor the objective measurement value (or equivalent spherical power) when the fogging amount is gradually increased to the positive side to confirm whether or not the lens eye of the subject eye E loosens before performing the subjective examination.

In Step S3, following the fogging control in Step S2, the objective refraction measurement (refraction measurement) is performed. The objective refraction measurement is performed by the following procedure. More specifically, the control portion 40 projects the ring measurement pattern onto the ocular fundus Ef of the fogged subject eye E by the refraction measurement projection system 6. The control portion 40 receives the refraction light of the ring measurement pattern from the ocular fundus Ef as the ring image as a ring image, and measures the spherical power, cylindrical power, and cylindrical axis angle as eye refractive power based on the image signal from the imaging element 59 with a known method.

In this case, when an examiner selects "objective examination" in the objective refraction measurement, the objective examination screen 8 is displayed on the display portion 32 of the examiner's controller 30. A subject eye display portion (right eye) 8*a*, a subject eye display portion (left eye) 8*b*, an objective refraction measurement result display portion (right eye) 8*c*, an objective refraction measurement result display portion (left eye) 8*d*, an alignment guide 8*e*, a pupil distance change/display portion 8*f*, a corneal apex distance display portion 8*g*, a driving reset button 8*h*, an examination target eye selection button 8*i*, a function button 8*j*, a measurement head height adjustment button 8*k*, and the like are displayed on the objective examination screen 8.

In Step S4, following the objective refraction measurement in Step S3, the refraction analysis is performed with the image of the ring image RI obtained by the objective refraction measurement. In the refraction analysis, the reliability coefficient SC based on the score value showing the high reliability is calculated for one item or the combination of a plurality of items of the characteristic amounts of the selected ring image RI.

In Step S5, following the refracting analysis in Step S4, it is determined whether or not the subjective test content includes the feedback for the analysis result of the characteristic amount of the ring image RI. More specifically, the reliability coefficient SC calculated in Step S4 is a normal determination value or more, it is determined that the subjective test content includes no feedback for the analysis result of the characteristic amount of the ring image RI, and the process proceeds to Step S7. On the other hand, when the reliability coefficient SC is less than the normal determination value, it is determined that the subjective test content includes the feedback for the analysis result of the characteristic amount of the ring image RI, and the process proceeds to Step S6.

In Step S6, following the determination of the feedback of the analysis result of the characteristic amount of the ring image RI in Step S5, an alert message is displayed on the subjective examination screen 9 displayed on the display portion 32 of the examiner's controller.

At the end of the analysis of the characteristic amount of the ring image RI, when an examiner switches "objective examination" to "subjective examination", the subjective examination screen 9 is displayed on the display portion 32 of the examiner's controller 30 to start the subjective refraction examination, as illustrated in FIG. 8. An operation panel 9*a*, a title display portion 9*b*, a main data display portion 9*c*, an optometric window (right eye) 9*d*, an optometric window (left eye) 9*e*, an emergency stop button 9*f*, a chart page display portion 9*g*, an examination distance display portion 9*h*, an alert message display portion 9*i*, a large chart display portion 9*j*, a function button 9*k*, and the like are displayed on the subjective examination screen 9. The alert message is displayed on the alert message display portion 9*i* of the subjective examination screen 9 that is easily recognized by an examiner in the subjective examination.

The display example of the alert message will be described. For example, when the reliability coefficient SC is low, in particular, the "contrast of ring image RI" is low, the feedback is determined. As the alert example of this case, an alert message "Low reliable objective refraction measurement result was obtained. The best eyesight may not be sufficient even though eyesight is corrected with the power of measurement result" is displayed.

For example, when the reliability coefficient SC is low, in particular, "Residual to approximate ellipse AE of detection point DP of ring image RI" is large, the feedback is determined. As an alert example of this case, an alert message "Low reliable objective refraction measurement result was obtained. It may be difficult to obtain corrected eyesight. Response of patient may not be intended in the examination of astigmatism power" is displayed.

In Step S7, following the determination of no feedback in Step S5 or the alert message display in Step S6, the subjective refraction examination is performed, and the process proceeds to END upon ending the subjective refraction examination.

The subjective refraction examination repeats the correction of the spherical power and the correction of the astigmatism power by changing the correction lens after the RG examination in one eye of the subject eyes, for example. When the eyesight value settles to the target value, the weakest power is obtained, and this power is set as the subjective refraction value of one eye. Next, the subject eye is changed, and the similar examination is repeated. After that, upon ending the examination of the right and left both eyes, the both eye balance examination is performed, and the subjective refraction value and the best eyesight value of the both eyes are recorded, and the subjective refraction examination ends.

Figure 6:
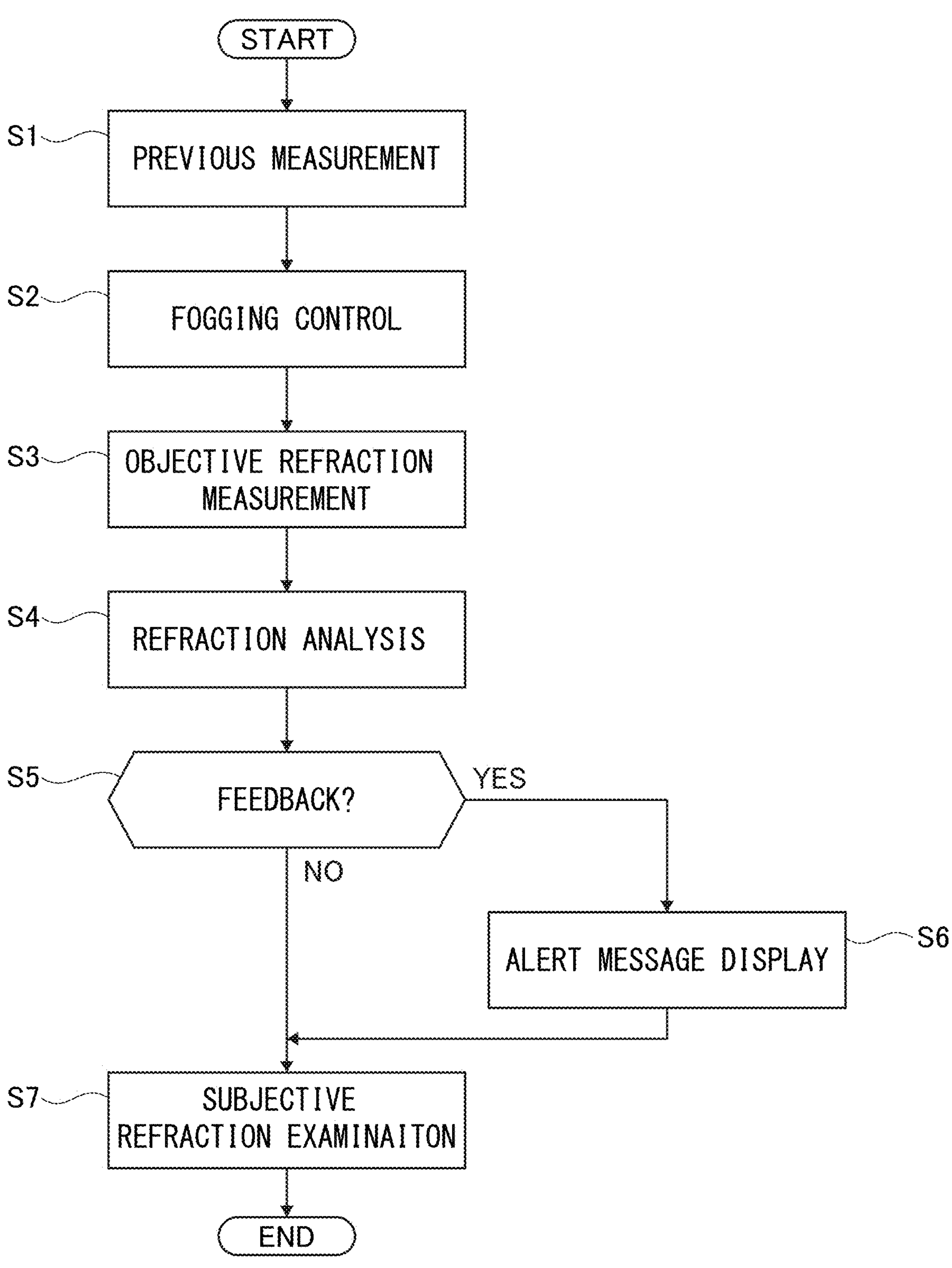
FIG. 6 is a flowchart illustrating a flow of a feedback control process that feedbacks a characteristic amount analysis result of the ring image of the subject eye to subjective examination in the first embodiment.
Figure 7:
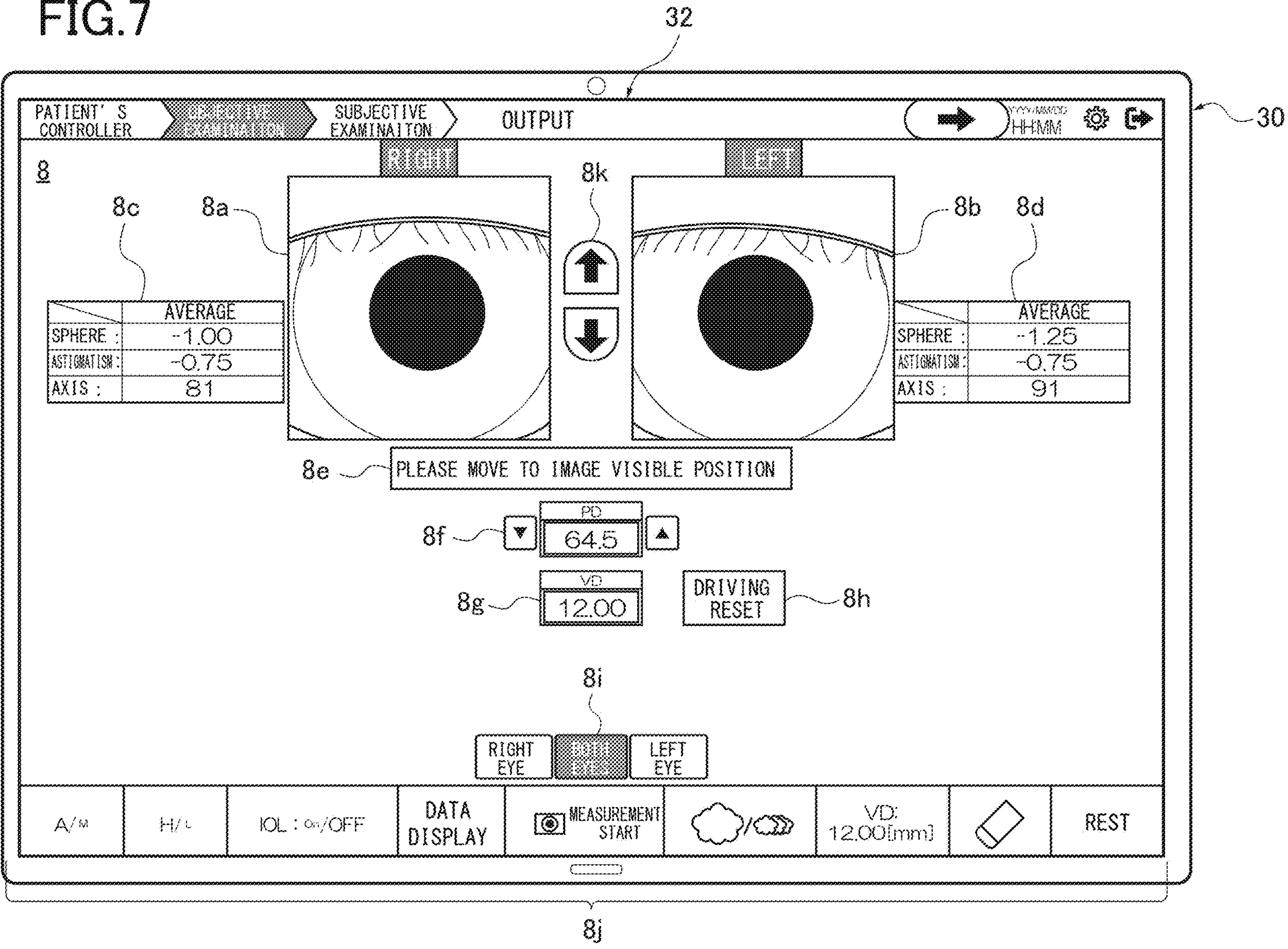
FIG. 7 is a view illustrating one example of an objective examination screen that is displayed on a display portion of an examiner's controller in objective examination.

As described above, the refraction analysis is performed, and when it is determined that the analysis result includes the feedback, in the flowchart of FIG. 6, the process proceeds S1→S2→S3→S4→S5→S6→S7. In Step S6, the alert message is displayed on the subjective examination screen 9 according to the analysis result of the characteristic amount of the ring image RI.

The feedback operation to the subjective examination content will be described. When the subject eye has abnormal eyes (e.g., cataract eye and high order aberration eye), a problem may be caused during the subject examination. For example, the best eyesight may be lower than that of normal subject eyes or the response to the astigmatism examination is no good in the subjective test. On the other, for example, in the objective measurement device with the subjective examination operation, the refraction value information by the spherical power, the astigmatism power, and the astigmatism axis angle obtained by the objective measurement are displayed on the subjective examination screen. However, an examiner cannot find a reason that the best eyesight cannot be obtained and the response to the astigmatism examination is irregular even from the refraction value information to be displayed on the subjective examination screen.

Accordingly, when the problem occurs during the subjective examination, it is necessary for the examiner to perform the examination without finding the reason for the problem. When finding the reason for the problem during the subjective examination, the objective measurement is re-performed to the subject eyes after the end of the subjective examination with the problem, and it is necessary to find the reason by analyzing the objective measurement result. It takes a time to find the reason.

With respect to the above background art, the solution that estimates a possibility (reliability) of the abnormal eyes of the subject eyes by analyzing the ring image RI obtained by the objective measurement to feedback to the subjective examination content based on the possibility. Herein, the analysis of the ring image RI is meant to analyze the contrast, width and the like of the ring image RI and a Root Mean Square (RMS) when ellipse approximating the ring image RI while paying attention to the problem that may occur in the subjective examination. As described above, when the refraction error is found in the subject eyes E in the objective measurement that is performed before the subjective examination, the subjective test content is feedback, so that it is possible to previously address the problem that may occur during the subjective examination.

In the first embodiment, as the feedback to the subjective examination content, just after the objective measurement or when performing the subjective examination, the alert message of the analysis result is displayed to an examiner. Accordingly, for example, when the "contrast of ring image RI" is low, a high possibility of the cloud of the intermediate transmission body is estimated. Based on this estimation, an alert message "Low reliable objective refraction measurement result was obtained. The best eyesight may be insufficient even though eyesight is corrected with the power of measurement result" is displayed. The examiner reads this displayed alert message, and finds the reason for the problem that the best eyesight of the patient cannot be obtained. As a result, the examiner who finds the reason for the problem in the subjective examination can smoothly proceed with the subjective examination.

For example, when "residual to approximate ellipse AE of detection point DP of ring image RI" is large, irregular astigmatism is highly estimated. Based on this estimation, an alert message "Low reliable objective refraction measurement was obtained. The corrected eyesight may not be obtained. Intended response of patient may not be obtained in examination of astigmatism power." is displayed. Accordingly, the examiner reads the displayed alert message to previously find the reason for the irregular case of the response of the patient in the examination of the astigmatism power or the reason for the case the corrected vision cannot be obtained. As a result, the examiner who finds the reason for the problem in the subjective examination smoothly proceeds with the subjective examination.

As described above, in the ophthalmologic apparatus A of the first embodiment, the following effects can be achieved.

(1) An ophthalmologic apparatus A includes an objective measurement optical system (refraction measurement projection system 6, refraction measurement light receiving system 7) that measures an objective refraction characteristic of a subject eye E and a control portion 40 that performs total control including control of the objective measurement optical system. The control portion 40 analyzes a characteristic amount of a ring image RI obtained by measuring the objective refraction characteristic of the subject eye E to feedback to a subjective examination content of the subject eye E according to an analysis result of the characteristic amount of the ring image RI. With this configuration, when the subject eye E has a refraction error, it is possible to previously respond to a problem that may occur during subjective examination.

(2) The control portion 40 displays an alert message of the analysis result just after objective measurement or when subjective examination is performed upon determination that the analysis result of the characteristic amount of the ring image includes feedback. With this configuration, when a problem occurs due to a case in which the best eyesight of the subject is not obtained in the subjective examination, a case in which the response of a subject in the examination of astigmatism power is irregular, and the like, an examiner who understands the cause of the occurrence of the problem in advance can suitably responds to the occurrence of the problem.

(3) The control portion 40 sets the characteristic amount of the ring image RI obtained by measuring the objective refraction characteristic to one item or combination of a plurality of items of brightness of the ring image RI, an edge intensity of the ring image RI, a contrast of the ring image RI, a width of the ring image RI, residual to an approximate ellipse AE of a detection point DP of the ring image RI, a number of detection points of the ring image RI, and a center coordinate PC of an approximate ellipse AE of a detection point DP of the ring image RI. With this configuration, it is possible to deal with a problem that an examiner wishes to understand in advance in subjective examination, and select the characteristic amount by the suitable number of items. As a result, for example, by selecting a plurality of characteristic amounts, it is possible to respond to an accurate requirement of understanding a reason for a problem, and also respond to a requirement that an examiner wishes to understand a problem pattern in advance as many as possible.

(4) The control portion 40 calculates a reliability coefficient SC based on a score value Z1-Z7 showing reliability in the subjective measurement for the one item or the combination of a plurality of items of the characteristic amounts of the ring image RI when analyzing the characteristic amount of the ring image RI obtained by measuring the objective refraction characteristic, and determines feedback to the analysis result of the characteristic amount of the ring image RI with comparison between the reliability coefficient SC and a normal determination value. With this configuration, the reliability coefficient SC showing reliability in the subjective examination is used as an index value for the feedback, and the feedback to the analysis result of the characteristic amount of the ring image RI in the subjective examination can be determined by the comparison between the reliability coefficient SC and the normal determination value.

Second Embodiment

The second embodiment is an example that changes an automatic optometry algorithm of a subjective examination to an algorithm in which an analysis result is reflected from a previously determined algorithm as feedback to a subjective examination content. Note that the configuration of the second embodiment is similar to the configuration of the first embodiment illustrated in FIGS. 1-3, and thus the description and the figure thereof will be omitted.

The feedback control process operation that feedbacks the characteristic amount analysis result of the ring image RI of the subject eye E to the subjective examination will be described with reference to FIG. 9. The subjective examination in the second embodiment is performed by the previously determined automatic optometry algorithm. Steps S1 to S5 in FIG. 9 are the same as those in FIG. 6, and thus, the description thereof will be omitted.

In Step S8, following the determination of no feedback of the analysis result of the characteristic amount of the ring image RI in Step S5, the correction of the spherical power of the subject eye E (first time) is performed. In Step S9, following the correction of the spherical power in Step S8 (first time), the correction of the astigmatism power of the subject eye E is performed. In Step S10, following the correction of the astigmatism power in Step S9, the correction of the spherical power of the subject eye E (second time) is performed, and the process proceeds to END. Note that (first correction of spherical power)→(correction of astigmatism power)→(second correction of spherical power) by the flow S8→S9→S10 correspond to one example of the previously determined automatic optometry algorithm in the subjective examination.

In Step S11, following the determination of the feedback of the analysis result of the characteristic amount of the ring image RI in Step S5, the correction of the spherical power of the subject eye E (first time) is performed. In Step S12, following the correction of the spherical power in Step S11 (first time), "visual performance of eye chart when correcting with astigmatism power of objective measurement value" is compared to "visual performance of eye chart without astigmatism power". When the corrected eyechart is clearly viewed, the process proceeds to Step S13, and when the eyechart without astigmatism power is clearly viewed, the process proceeds to Step S14. In Step S13, following the determination of the clear view of the eye chart when corrected in Step S12, the correction of the astigmatism power of the subject eye E is performed. In Step S14, following the determination of the clear view of the eye chart without astigmatism power or the correction of the astigmatism power in Step S13, the correction of the spherical power of the subject eye E (second time) is performed, and the process proceeds to END. Note that the flow that skips Step S13, i.e., Step 11→Step S12→Step 14 without the correction of the astigmatism power corresponds to a change example of the previously determined automatic test algorithm in the subjective examination.

Figure 9:
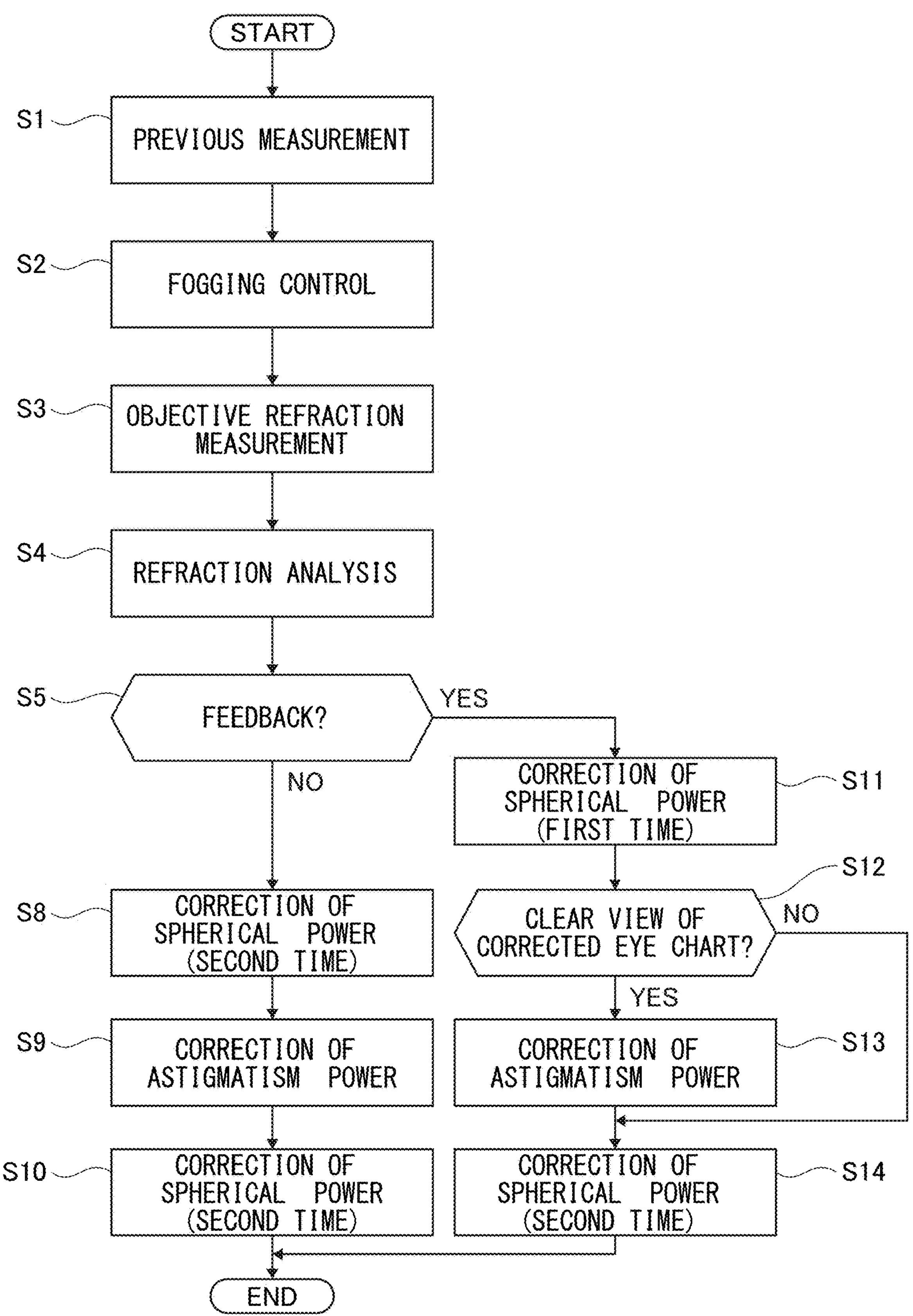
FIG. 9 is a flowchart illustrating a flow of a feedback control process that feedbacks a characteristic amount analysis result of a ring image of a subject eye to subjective examination in the second embodiment.

As described above, the refraction analysis is performed, and when it is determined that the analysis result includes the feedback, and when the visual performance of the eyesight is better without the astigmatism power than that of the correction, in the flowchart of FIG. 9, the process proceeds to S1→S2→S3→S4→S5→S11→S12→S14. The automatic optometry algorithm of the subjective examination is changed to the algorithm that skips the correction of the astigmatism power.

The feedback operation to the subjective examination content will be described. When the subjective examination is performed by the previously determined automatic optometry algorithm, if the subject eye has an abnormal eye (e.g., cataract eye and high order aberration eye), the astigmatism power during the automatic optometry may not be corrected, which reads to an algorithm error that cannot proceed to next procedure.

On the other hand, in the second embodiment, as the feedback to the subjective examination content, the automatic optometry algorithm is changed to the content in which the analysis result of the characteristic amount of the ring image RI is reflected, and the subjective examination by the changed algorithm is performed. Accordingly, the algorithm error that cannot proceed to the next procedure during the automatic examination is prevented, and the frequency of the error case is lowered compared to the case when the automatic optometry algorithm is not changed regardless of the analysis result.

As described above, in the ophthalmologic apparatus A of the second embodiment, the following effects can be achieved in addition to the effects (1), (3), (4) of the first embodiment.

(5) The control portion 40 performs subjective examination with a previously determined automatic optometry algorithm upon determination that the analysis result of the characteristic amount of the ring image RI includes no feedback, and changes the automatic optometry algorithm to a content in which the analysis result of the characteristic amount of the ring image RI is reflected upon determination that the analysis result of the characteristic amount of the ring image includes feedback. With this configuration, in the subjective examination with an automatic optometry mode, the frequency of an error case can be reduced compared to a case in which an automatic optometry algorithm is not changed regardless of the analysis result.

Moreover, in the first embodiment, when the analysis result of the characteristic amount includes the feedback, the visual performance of the eyechart when the astigmatism power is corrected is compared to the visual performance of the eye chart when the astigmatism power is not corrected without skipping the correction of the astigmatism power.

Figure 10:
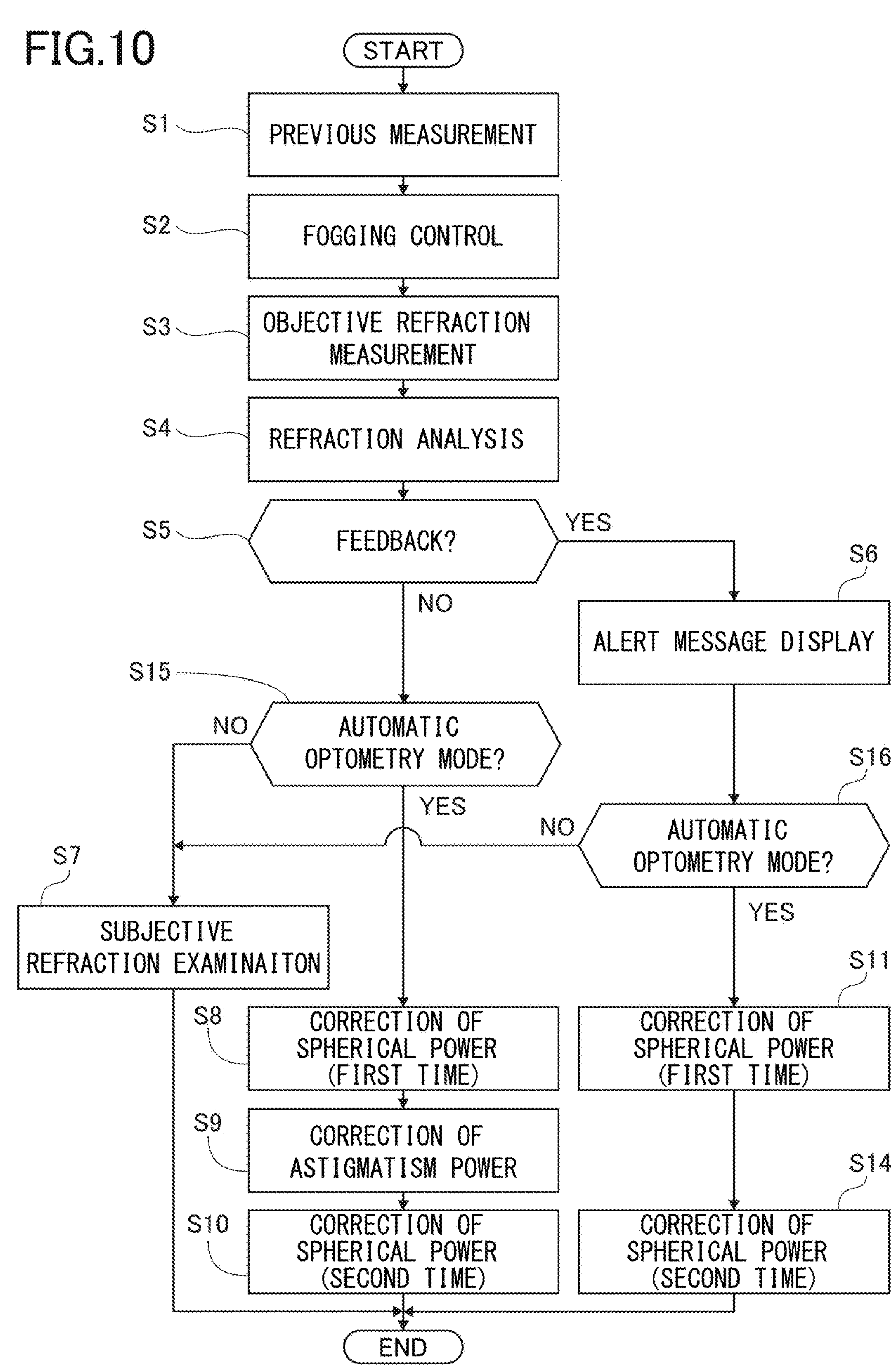
FIG. 10 is a flowchart illustrating a flow of a feedback control process that feedbacks a characteristic amount analysis result of a ring image of a subject eye to subjective examination in a modified example of the second embodiment.

A modified example of the second embodiment will be described. The feedback control process operation that feedbacks the characteristic amount analysis result of the ring image RI of the subject eye E to the subjective examination will be described with reference to FIG. 10. The subjective examination by the modified example of the second embodiment can select the manual optometry mode and the automatic optometry mode by an examiner. Steps S1 to S7 in FIG. 10 are the same as Steps S1 to S7 in FIG. 6, and Steps S8 to S11, S14 in FIG. 10 are the same as Steps S8 to S11, S14 in FIG. 9, and thus, the description thereof will be omitted.

In Step S15, the following determination of no feedback of the analysis result of the characteristic amount of the ring image RI in Step S5, it is determined wither or not it is the automatic optometry mode. When it is the automatic optometry mode, the process proceeds to after Step S8 (process with normal automatic optometry algorithm), and when it is the manual optometer mode, the process proceeds to Step S7.

In Step S16, following the display of the alert message in Step S6, it is determined whether or not it is the automatic optometry mode. When it is the automatic optometry mode, the process proceeds after Step S11 (process with automatic optometry algorithm after change). The process with the automatic optometry algorithm after the change during the subjective examination is a process that skips the correction of the astigmatism power.

As described above, in the modified example of the second embodiment, as the feedback to the subjective examination content, the display of the alert message and the change in the automatic optometry algorithm are used. Accordingly, both of the effects (1) to (4) of the first embodiment and the effect (5) of the second embodiment are achieved.

Third Embodiment

Figure 11:
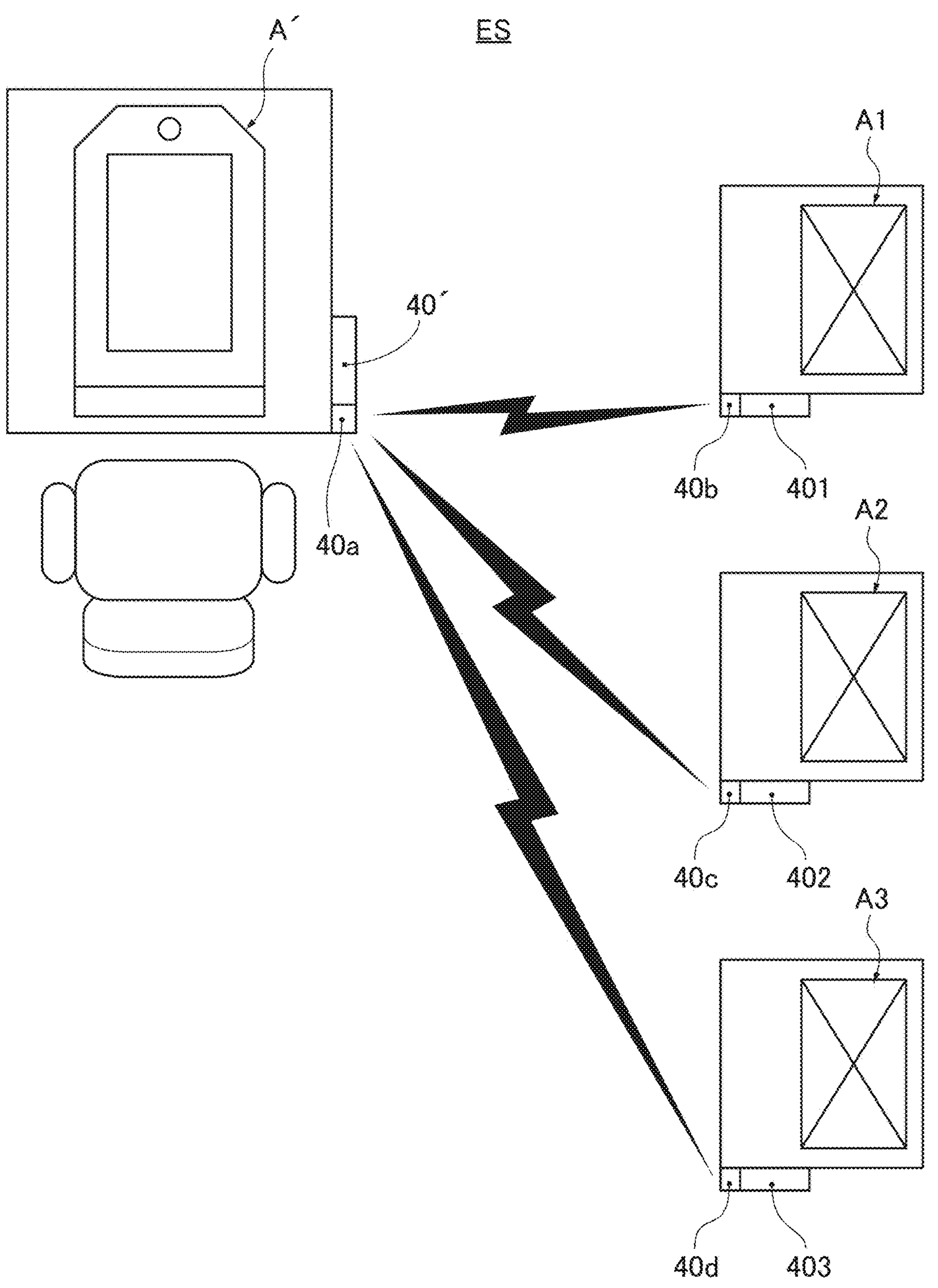
FIG. 11 is a schematic view illustrating an ophthalmologic system including an objective measurement device and a plurality of subjective examination devices as one example of the ophthalmologic apparatus.

The third embodiment is an application example to an ophthalmologic system including an objective measurement device and at least one subjective examination device that performs a subjective examination. The ophthalmologic system of the third embodiment will be described with reference to FIG. 11.

The third embodiment relates to an ophthalmologic system ES including one objective measurement device A' that measures the objective refraction characteristic of the subject eye E and three subjective examination devices A1, A2, A3 that perform the subjective examination that obtains the subjective refraction value of the subject eye E. A control portion 40' of the objective measurement device A' adopts a configuration that shares information by sending the feedback content to the control portions 401, 402, 403 of the subjective examination devices A1, A2, A3 when the feedback content is determined according to the analysis result of the characteristic amount of the ring image RI. In this case, the control portion 40' and the control portions 401, 402, 403 can exchange the information with wireless communication by disposing transceivers 40*a*, 40*b*, 40*c*, 40*d*. Wired connection with a two-way communication line, for example, may be used instead of the wireless communication or the wireless communication and the wired connection may be combined.

The control portion 40' of the objective measurement device A' analyzes the characteristic amount of the ring image RI obtained by measuring the objective refraction characteristic of the subject eye E, and determines the subjective examination content according to the analysis result of the characteristic amount of the ring image RI. The control portion 40' shares the operation that sends the determined subjective examination content to the control portions 401, 402, 403 of the subjective examination devices A1, A2, A3.

The subjective examination devices A1, A2, A4 share the different examination types of the subjective examination, respectively. When the subjective examination devices A1, A2, A3 receive the subjective examination content sent from the objective measurement device A', the subjective examination devices A1, A2, A3 display the alert message as the first embodiment in the subjective examination with the received subjective examination content as the feedback information, and change the automatic optometry algorithm as the second embodiment.

The ophthalmologic system ES of the third embodiment achieves the following effects in addition to the effects (1) to (5) of the first and second embodiments.

(6) The ophthalmologic apparatus independently includes, as the ophthalmologic apparatus, an objective measurement device A' that measures an objective refraction characteristic of the subject eye E and at least one subjective examination device A1, A2, A3 that performs subjective examination for obtaining a subjective refraction value of the subject eye E. The control portion 40' of the objective measurement device A' shares information by sending the feedback content to control portions 401, 402, 403 of the subjective examination devices A1, A2, A3 upon determination of the feedback content according to the analysis result of the characteristic amount of the ring image RI. With this configuration, when it is recognized that the subject eye E has a refraction error by the analysis of the characteristic amount of the ring image RI in the objective measurement device A', the ophthalmologic system ES that previously respond to a problem that may occur during the subjective examination in the subjective examination device A1, A2, A3 that shares information can be provided.

As described above, the ophthalmologic apparatus of the present disclosure is described based on the first, second, and third embodiments. However, the detailed configuration is not limited to these embodiments, and for example, the change in and the addition to the design are allowed without departing from the scope of the invention according to each claim.

The first embodiment describes an example that displays the alert message on the subjective examination screen 9 as the feedback example to the subjective examination content when the feedback is determined based on the analysis of the ring image RI. However, when the feedback is determined based on the analysis of the ring image, the alert message may be displayed on both of the objective measurement screen and the subjective measurement screen as the feedback example to the subjective examination content. When the alert message is displayed, a voice alert message may be used.

The first embodiment describes an example that does not display the alert message on the subjective examination screen 9 when no feedback is determined based on the analysis of the ring image RI. However, as the feedback example to the subjective test content even when no feedback is determined based on the analysis of the ring image, a message such as "High reliable objective refraction measurement result was obtained" may be displayed as the feedback example to the subjective measurement content.

The first embodiment describes an example that displays the alert message of the analysis result as the feedback to the subjective examination content. The second embodiment describes an example that changes the automatic optometry algorithm based on the analysis result. However, as the feedback to the subjective examination content, the example that uses both of the display of the alert message of the analysis result and the change in the automatic optometry algorithm based on the analysis result is adopted as the feedback to the subjective examination content, as described in the modified example of the second embodiment.

The first and second embodiments describe an example that determines the feedback based on the comparison between the reliability coefficient SC with the score values Z1 to Z7 showing the reliability in the subjective examination and the normal determination value for the item of the characteristic amount of the ring image RI when analyzing the characteristic amount of the ring image RI. However, an analysis example that recognizes an image with a method of deep learning the ring image, and determines the feedback content by the image recognition result when analyzing the characteristic amount of the ring image may be used. The deep learning is one of the mechanical learning methods using a neural network of multilayer structure that reproduces a structure of a nerve cell of a human, and is good at image recognition and voice recognition and has a merit that automatically extracts the characteristic amount. When highly accurate analysis is achieved by adopting the deep learning to the characteristic amount analysis, it is necessary to previously collect many data sets that connect the ring image and the problem contents in the subjective examination.

The first and second embodiments describe an example that is applied to the ophthalmologic apparatus A that is both eye open type capable of objectively measuring the eye characteristic of the left and right subject eyes and has the objective measurement device having the subjective examination function. However, the ophthalmologic apparatus is not limited thereto, and may be applied to an ophthalmologic apparatus of a single eye type having an objective measurement optical system that objectively measures the characteristic of the left subject eye and the characteristic of the right subject eye one by one. The ophthalmologic apparatus may be applied to the objective measurement apparatus of the both eye open type or the single eye type having only the objective measurement optical system.

What is claimed is:

1. An ophthalmologic apparatus comprising: an objective measurement optical system that measures an objective refraction characteristic of a subject eye; and a control portion that performs total control including control of the objective measurement optical system, wherein the control portion analyzes a characteristic amount of a ring image obtained by measuring the objective refraction characteristic of the subject eye to feedback to a subjective examination content of the subject eye according to an analysis result of the characteristic amount of the ring image, and wherein the control portion performs subjective examination with a previously determined automatic optometry algorithm upon determination that the analysis result of the characteristic amount of the ring image includes no feedback, and changes the automatic optometry algorithm to a content in which the analysis result of the characteristic amount of the ring image is reflected upon determination that the analysis result of the characteristic amount of the ring image includes feedback, wherein a determination of no feedback results from the analysis result of the characteristic amount of the ring image determining that the subject eye has a low probability of ametropia in the subject eye in an extent to cause an error in automatic subjective examination, and wherein a determination of feedback results from the analysis result of the characteristic amount of the ring image determining that the subject eye has a high probability of ametropia in the subject eye in the extent to cause the error in automatic subjective examination.

2. The ophthalmologic apparatus according to claim 1,
wherein the control portion displays an alert message of the analysis result just after objective measurement or when subjective examination is performed upon determination that the analysis result of the characteristic amount of the ring image includes feedback.

3. The ophthalmologic apparatus according to claim 1,
wherein the control portion sets the characteristic amount of the ring image obtained by measuring the objective refraction characteristic to one item or combination of a plurality of items of brightness of the ring image, an edge intensity of the ring image, a contrast of the ring image, a width of the ring image, residual to an approximate ellipse of a detection point of the ring image, a number of detection points of the ring image, and a center coordinate of an approximate ellipse of a detection point of the ring image.

4. The ophthalmologic apparatus according to claim 3,
wherein the control portion calculates a reliability coefficient based on a score value showing reliability in the subjective measurement for the one item or the combination of a plurality of items of the characteristic amounts of the ring image when analyzing the characteristic amount of the ring image obtained by measuring the objective refraction characteristic, and determines feedback to the analysis result of the characteristic amount of the ring image with comparison between the reliability coefficient and a normal determination value.

5. The ophthalmologic apparatus according to claim 1 further comprising, as the ophthalmologic apparatus, an objective measurement device that measures an objective refraction characteristic of the subject eye and at least one subjective examination device that performs subjective examination for obtaining a subjective refraction value of the subject eye, wherein the control portion of the objective measurement device shares information by sending the feedback content to a control portion of the subjective examination device upon determination of the feedback content according to the analysis result of the characteristic amount of the ring image.

6. The ophthalmologic apparatus according to claim 1, wherein the characteristic amount is a function of one or more scores assigned to corresponding objective refractive characteristics derived from the ring image.

7. The ophthalmologic apparatus according to claim 6, wherein the objective refractive characteristics are selected from a brightness of the ring image, an edge intensity of the ring image, a contrast of the ring image, a width of the ring image, residual to an approximate ellipse of a detection point of the ring image, a number of detection points of the ring image, and a center coordinate of an approximate ellipse of a detection point of the ring image.

8. The ophthalmologic apparatus according to claim 6, wherein no feedback is determined upon determining that the characteristic amount of the ring image is on a normal side of a threshold, otherwise feedback is assigned.

* * * * *